US00PP10142P

United States Patent [19]

Ackerman

[11] Patent Number: Plant 10,142

[45] Date of Patent: Dec. 9, 1997

[54] VARIETY OF RASPBERRY NAMED 'PS-1049'

[75] Inventor: Stephen M. Ackerman, Salinas, Calif.

[73] Assignees: Plant Sciences, Inc.; Berry R & D, Inc., both of Watsonville, Calif.

[21] Appl. No.: 690,930

[22] Filed: Aug. 1, 1996

[51] Int. Cl.[6] ..... A01H 5/00

[52] U.S. Cl. ..... Plt./46.2

[58] Field of Search ..... Plt./46.2

*Primary Examiner*—James R. Feyrer

*Attorney, Agent, or Firm*—Christie, Parker & Hale, LLP

[57] ABSTRACT

Described is a new and distinct fall bearing red raspberry variety named 'PS-1049' which is capable of producing fruit on first year primocanes, and both floricanes and primocanes in subsequent years. The new variety is particularly characterized by its heavy primocane production, beginning as early as July 15 in Santa Cruz County, Calif., and significant floricane yields peaking in mid to late June. The fruit is of medium size with druplets of uniform size and distribution. The fruit is of excellent quality adapted well to the fresh fruit market with only a slight tendency to darken after harvest. The plant is vigorous with dense foliage and many stout thorns. The foliage is relatively large with an occasional raised mid vein and slight downward cupping.

3 Drawing Sheets

BACKGROUND OF THE INVENTION

The present invention relates to a new and distinct fall-bearing red raspberry variety which is the result of a cross between the variety designated 'PS-127' (U.S. Plant Pat. No. 7,437) and the variety known as 'Watson' (U.S. Plant Pat. No. 7,067). The variety is botanically known as *Rubus idaeus* and the varietal name is 'PS-1049'.

This variety of raspberry resulted from a breeding program with the objective of developing new and distinct raspberry varieties. The seedling resulting from the aforementioned cross was asexually propagated by dormant canes in a nursery located in Santa Cruz County, Calif., and was subsequently selected from a controlled breeding plot near Watsonville, Calif., in 1990. After its selection, the new variety was further asexually propagated in Santa Cruz County, Calif., by dormant canes and roots and non-dormant root shoot cuttings and extensively tested over the next several years in fruiting fields near Watsonville, Calif. This propagation and reproduction has demonstrated that the combination of traits disclosed herein as characterizing the new variety are fixed and remain true to type through successive generations of asexual reproduction.

SUMMARY OF THE INVENTION

Among the novel characteristics of the new variety are:

1. fall bearing of red raspberries;

2. capable of producing fruit on first year primocanes;

3. medium size fruit with druplets of substantially uniform size on distribution; and 4. vigorous plant habit with relatively large, dense foliage.

BRIEF DESCRIPTION OF THE ILLUSTRATIONS

The accompanying description and photographs describe typical specimens of the new variety at various stages of development as nearly true as it is possible to make in color reproductions of this character. Phenotypic expression may vary with differences in growth, environmental, and cultural conditions. Color terminology follows the Munsell Book of Colors, Munsell Color, Baltimore, Md., (1976).

Figure 1:
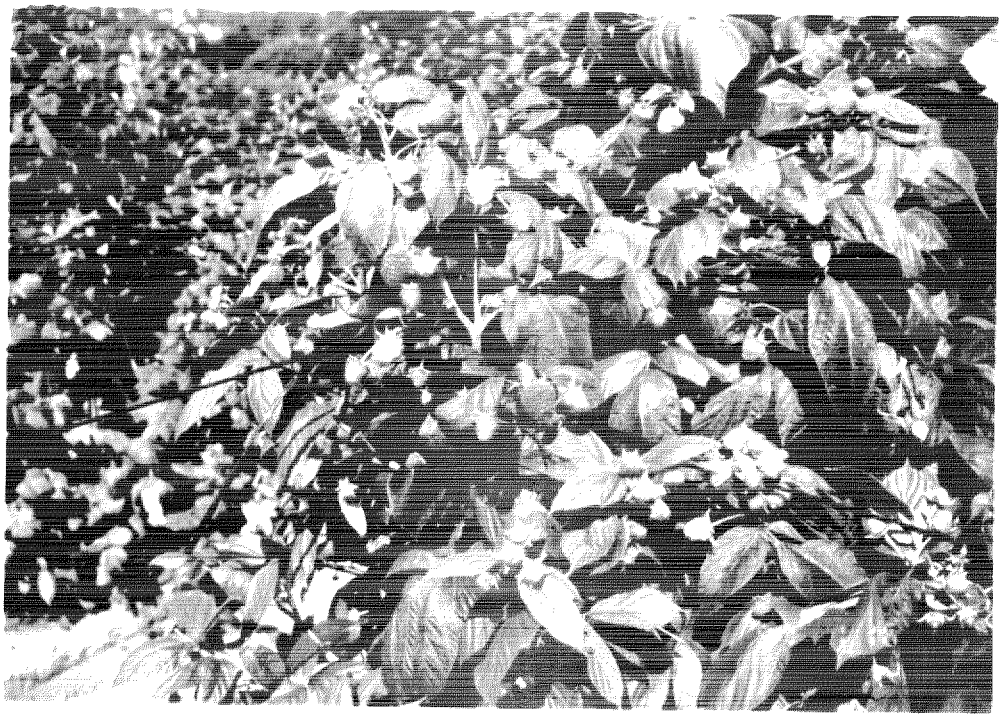
FIG. 1 shows a typical fruiting terminal and development stages from flower to mature fruit.
Figure 2:
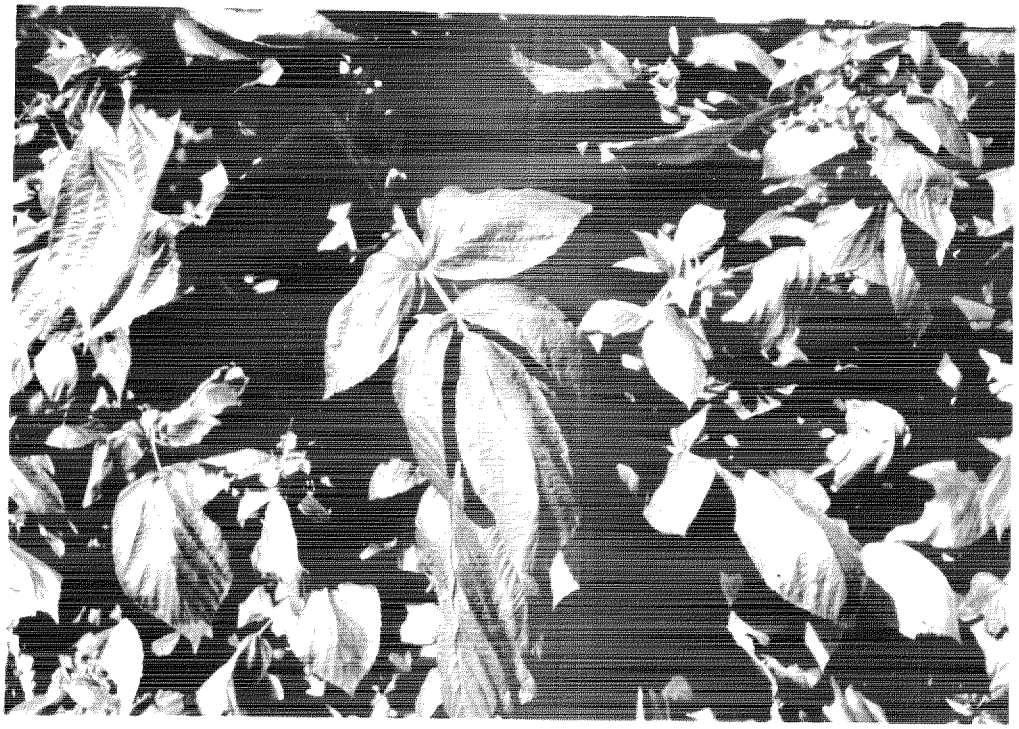
FIG. 2 shows a typical mature leaf and leaflets depicting a raised mid-vein, and typical veination.
Figure 3:
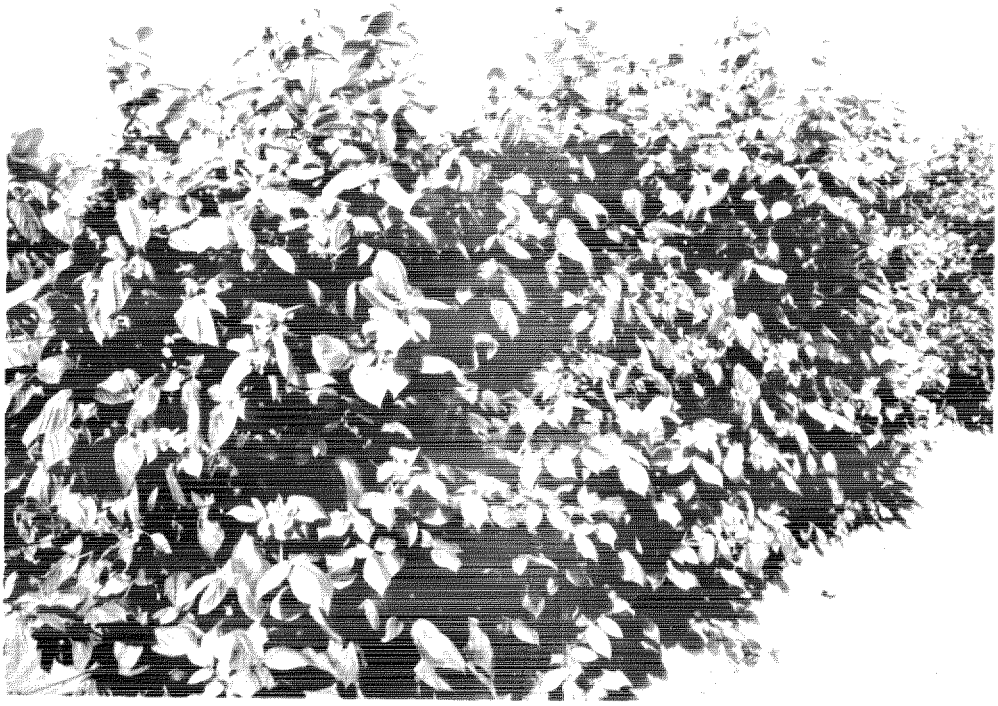
FIG. 3 shows typical plant growth habits and fruiting characteristics.
Figure 4:
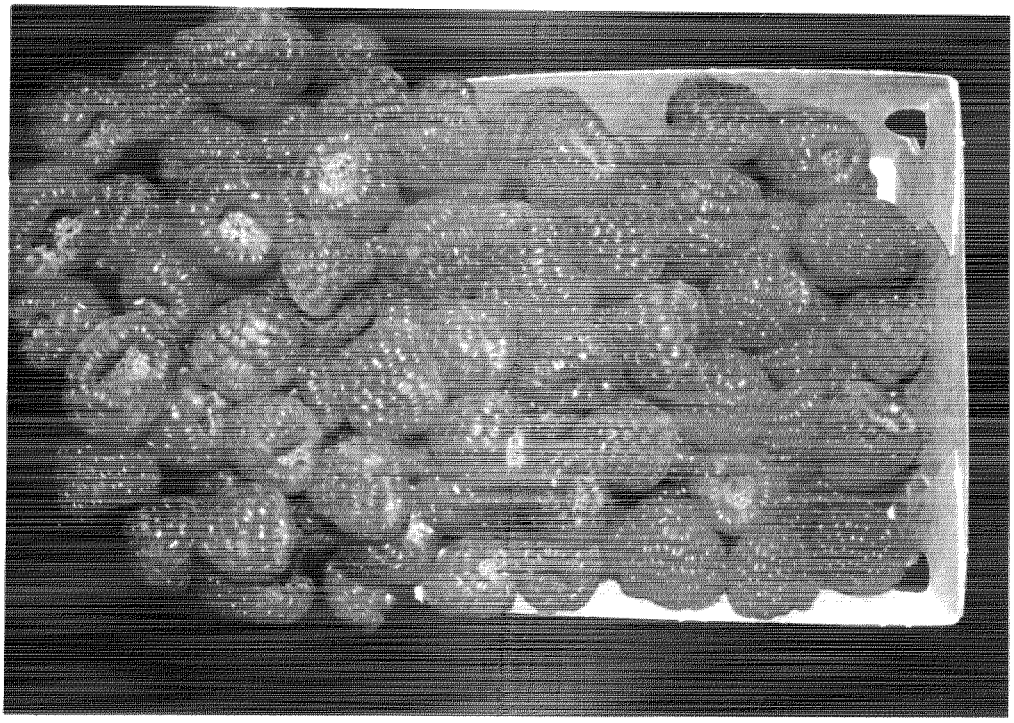
FIG. 4 shows typical fruit.
Figure 5:
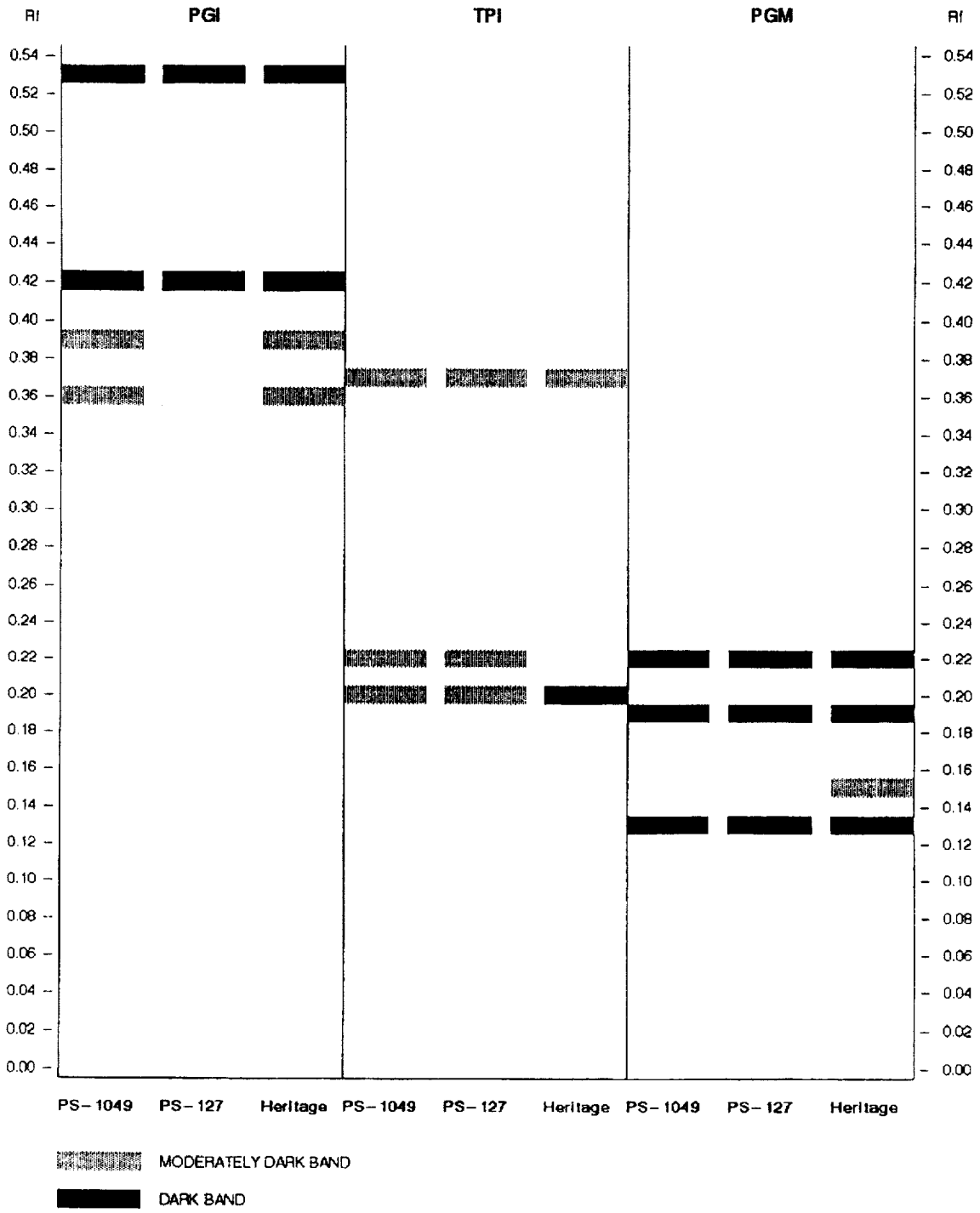

FIG. 5 discloses the isozyme banding patterns for 'PS-1049' compared with those of 'PS-127' and 'Watson'.

DESCRIPTION OF THE NEW VARIETY

'PS-1049' is primarily adapted to the climate and growing conditions of the central coast of California. This region provides desirable year-round temperatures to produce a strong vigorous plant, and to remain in fruit production from about July through December and, in the ensuing year from May through July. The nearby Pacific ocean provides humidity and cool temperatures to maintain fruit quality during the summer production months. The new variety has also demonstrated its adaptation to the growing systems and styles of the San Diego, Calif. district, e.g. the planting of dormant canes and roots in mid summer for fall and winter (i.e. October–March) fruit production.

'PS-1049' is a vigorous plant with dense deciduous foliage when provided with optimum chilling in the nursery propagation fields prior to being dug, and artificial cold storage prior to being planted. The plant of the new variety is shorter yet denser than 'Heritage' and taller than 'PS-127'. The plant is also more upright and erect in growth habit than 'Heritage' with a larger primocane basal diameter than both 'PS-127' and 'Heritage'. 'PS-1049' has more thorns per cane than 'PS-127' and fewer than 'Heritage'. Thorns are longer, stronger and more stout than 'PS-127'. Table 1 summarizes primocane characteristics of 'PS-1049', 'PS- 127' and 'Heritage'.

TABLE 1

Comparison of primocane plant characteristics of 'PS-1049', 'PS-127' and 'Heritage' from Watsonville, California, August 22, 1995.

| CHARACTER | 'PS-1049' | 'PS-127' | 'Heritage' |
|---|---|---|---|
| Musell Color primocane | 5GY-7/4 to 5GY-6/4 | 5GY 7/4 to 5GY 6/4 | 2.5 GY 7/6 to 2.5GY 6/6 |
| Primocane Length mean (m) | 1.8 | 1.6 | 2.0 |
| Lateral Length mean | 44.1 | 60.3 | 41.6 |

TABLE 1-continued

Comparison of primocane plant characteristics of 'PS-1049', 'PS-127' and 'Heritage' from Watsonville, California, August 22, 1995.

| CHARACTER | 'PS-1049' | 'PS-127' | 'Heritage' |
|---|---|---|---|
| (cm) | | | |
| Primocane Basal diameter mean (mm) | 18.3 | 16.4 | 16.3 |
| Primocane Internode length mean (cm) | 4.3 | 4.5 | 3.2 |
| Thorn Length mean (mm) | 2.0 | 0.8 | 2.2 |
| Thorns per cm mid-cane mean | 3.4 | 2.2 | 4.4 |

The foliage of the new variety is lighter in color than 'Heritage' yet similar in color with less gloss than 'PS-127'. The leaves are larger, less rounded and less cupped than 'PS-127' yet similar in shape and appearance to 'Heritage'. Leaflets have a slightly raised mid vein similar to 'Heritage' which 'PS-127' lacks.

'PS-1049' is capable of long season fruit production with fruit of good size and excellent quality during the entire season when provided with optimum chilling in the nursery propagation fields, and artificial cold storage, prior to being planted. Primocane fruit production of 'PS-1049' begins as early as about mid July, earlier than both 'PS-127' and 'Heritage' with a heavier July–August crop than 'PS-127' but similar to 'Heritage'. 'PS-1049' primocane fruit production peaks from about late August to early September, as much as 3 weeks earlier than 'PS-127'. Primocane production of 'PS-1049° may continue into November if rains and cold temperatures do not prevent the harvest with a heavier total yield than both 'PS-127' and 'Heritage'. Table 2 and 3 summarizes fruit production and fruit characteristics for 'PS-1049', 'PS-127' and 'Heritage'.

TABLE 2

1993–1994 market fruit yield and fruit size characteristics from plants harvested from July through November 1993 (fall) and May through July 1994 (spring) of 'PS- 1049' compared with standard cultivars dug December 9, 1993 and planted January 11, 1994 in Watsonville, California

| CHARACTER | 'PS-1049' | 'PS-127' | 'HERITAGE' |
|---|---|---|---|
| Fall Yield July–August gm/pl | 573 | 327 | 574 |
| Fall Yield Total gm/pl | 2007 | 1197 | 1522 |
| Spring Yield May gm/pl | 293 | 746 | 22 |
| Spring Yield July gm/pl | 430 | 154 | 466 |
| Spring Yield total gm/pl | 1611 | 1661 | 1048 |
| Average Fruit size fall means (gms) | 2.9 | 2.9 | 2.8 |
| Average Fruit size spring mean (gms) | 2.1 | 2.4 | 2.0 |

TABLE 3

Comparison of fruit characteristics of 'PS- 1049', 'PS- 127' and 'Heritage' from Watsonville, California, August 22, 1995

| CHARACTER | 'PS-1049' | 'PS-127' | 'HERITAGE' |
|---|---|---|---|
| Munsell Color fresh fruit | 5R 3/6 to 5R 3/8 | 7.5R 3/8 to 7.5R 3/10* | |
| Fruit Length mean (cm) | 2.1 | 2.2 | 2.1 |
| Fruit Width mean (cm)** | 1.9 | 1.8 | 1.9 |
| Seeds per Berry mean | 109 | 91 | 124 |
| Seed Weight mean (mgs)*** | 1.37 | 1.62 | 1.33 |

*'PS-127' fruit color according to Ackerman, U.S. Plant Pat. No. 7,437.
**Width was measured across the widest part of the berry, typically across the shoulders.
***Seed weight is measured after drying for 48 hours at room temperature.

Floricane fruit production of 'PS-1049' begins as early as the first of May, as much as 2 weeks earlier than 'Heritage' but similar to 'PS-127' with a heavier May crop than 'Heritage' but lighter than 'PS-127'. 'PS-1049' floricane production peaks from about mid to late June, as much as 2 to 3 weeks later than 'PS-127' and up to 1 week earlier than 'Heritage' with greater July yields than 'PS-127' and a heavier total floricane yield than 'Heritage'. Primocane season average fruit of 'PS-1049' is similar to both 'PS-127' and 'Heritage' with a smaller floricane season average fruit size than 'PS-127'.

The fruit of PS-1049' is more uniformly shaped than 'PS-127' with better overall appearance, firmness and gloss than both 'PS-127' and 'Heritage'. Table 4 summarizes fruit quality performance ratings. The fruit color of 'PS-1049' is noticeably lighter producing less of a waxy halo on the upper exposed surface than 'Heritage'. Druplets are more uniformly sized and arranged around the surface of the berry as compared to 'PS-127'.

TABLE 4

Comparison of fall fruit quality characteristics of 'PS-1049', 'PS-127' and 'Heritage'*

| CHARACTER | 'PS-1049' | 'PS-127' | 'HERITAGE' |
|---|---|---|---|
| Skin Firmness | 8.7 | 8.1 | 7.9 |
| Fruit Appearance | 8.2 | 7.0 | 7.2 |
| Fruit Gloss | 7.0 | 6.7 | 4.9 |

*Results are an average from 3 years of replicated holding tests performed from August through October of 1993 to 1995 in Watsonville, California. Ratings are based on a scale from 1–10; the higher the rating the stronger the skin and more attractive and glossy the berry.

The following further describes 'PS-1049', including the variety's morphological, electrophoretic, pest and disease reaction characteristics. This detailed description is based on observations taken during the spring and summer of 1995 in fruiting fields near Watsonville, Calif. Some characteristics were rated at different times in which case the date of the evaluation is listed. These measurements and ratings were made from plants dug from a nursery located in Santa Cruz County, Calif., in November 1994 and planted as dormant root stock in December 1994. The phenotypic characteristics of the new variety may vary slightly, depending upon variations in environmental factors, including weather (temperature, humidity and light intensity), day length, soil type and location without any change in the genotype of the plant. 'PS-1049' has not been observed under all possible environmental conditions. It has also not been tested for winter hardiness.

Fruit Characteristics

The fresh fruit of 'PS-1049' is medium red in color at maturity, color near 5R 3/6 to 5R 3/8. Mature fruit has a tendency to only darken slightly after 4–5 days of cold storage (1.1 degrees centigrade) to a color near 5R 2/4 to 5R 2/6. The fruit is moderately glossy with only a slight tendency to develop a waxy halo over its exposed upper surface. The mature fruit is very firm with very good appearance. At maturity, the fruit is weakly attached to the receptacle separating easily from the receptacle. The fruit cavity is medium in size and funnel shaped. The receptacle is conic in shape with a blunt tip and a tendency to split prior to the maturity of the fruit. Ripening fruit also has a tendency to split prior to maturity. The fruit possesses acceptable flavor and very good shipping qualities desirable for the fresh fruit markets.

Plant Characteristics

The primocane fruit is medium in size and characteristically conic in shape. The fruit is typically longer than wide with a moderate number of small to medium sized druplets. The druplets are evenly distributed around the berry and typically held even to the surface giving the berry a smooth textured surface. The druplets forming the berry collar at the open end fit tightly together forming a uniform ring of druplets.

The primocanes of 'PS-1049' are vigorous, of erect habit, with dense deciduous foliage. The plant crown produces from 1 to 6 primocane shoots per crown during the growing season and fruits on approximately the upper ⅓ of the cane. Primocanes are large in diameter, average from about 18.3 mm at the base to about 10.9 mm at approximately mid cane. Internodes are of medium length averaging about 4.3 cm in length.

The primocanes are light green in color, color near 5GY 7/4 to 5GY 6/4 with a thick waxy coat covering the outer surface of the cane. Primocanes produce many erect lateral branches on the upper third of the cane. A moderate number of strong and stout thorns are present on the canes. Thorn density is greater on about the basal ⅓ of the cane as compared to the upper portion of the cane. The thorn tips are held in a horizontal position relative to the cane axis. The basal thorn color is similar to the cane, color near 5GY 7/4 to 5GY 6/4 with a reddish purple tip, color near 7.5RP 3/6.

Floricanes are medium brown in color, color near 5YR 4/4 to 5YR 4/6 with a moderate number of lateral branches per cane. Floricanes also tend to have a waxy outer coat, medium grayish in color, color near 5YR 6/1 to 5YR 7/1.

Foliage Characteristics

'PS-1049' foliage characteristics are compared to those of 'PS-127' and 'Heritage' in Table 5.

TABLE 5

Comparison of leaf characteristics of 'PS-1049', 'PS-127' and 'Heritage' from Watsonville, California, August 22, 1995

| CHARACTER | 'PS-1049' | 'PS-127' | 'HERITAGE' |
|---|---|---|---|
| Munsell Leaf Color (upper surface) | 7.5GY 3/4 to 7.5GY 4/4 | 7.5GY 3/4 to 7.5GY 4/4 | 7.5GY 3/4 to 7.5GY 2/4 |
| Terminal Leaflet length mean (cm)* | 15.7 | 13.3 | 15.8 |
| Terminal Leaflet width mean (cm)* | 11.2 | 11.2 | 9.6 |
| Terminal Leaflet ratio (L/W)* | 1.40 | 1.18 | 1.66 |
| Petiole Length mean (cm) | 6.1 | 5.3 | 6.5 |
| Petiole Width mean (mm) | 3.2 | 3.5 | 3.0 |
| Petiolule Length mean (mm) | 4.4 | 5.0 | 4.2 |

*Terminal leaflets measurements are taken from a 3 leaflet leaf.

Mature leaves are a medium greenish yellow in color, color near 7.5GY 3/4 to 7.5 GY 4/4 on the upper surface and a pale greenish yellow color, color near 5GY 7/2 to 5GY 6/2 on the underside. Leaves are compound with typically an equal number of 3 and 5 leaflets per leaf. The terminal leaflets are cordate in shape tapering to an acuminate tip with many small shallow serrations. Serrations are present on all leaflets. Terminal leaflets are also relatively large in size and much longer than wide as described by the length/width ratio. Lateral leaflets are opposite. The upper surface of the leaf is non-glossy. Leaf veins are moderate with an occasionally raised mid vein and slight downward cupping. Petioles are a light greenish yellow color, color near 5 GY 7/8 to 5 GY 8/8 medium in length and thickness with a non waxy surface. Thorns are present averaging about 10.8 thorns per petiole.

Flowers

Flowers are medium in size, self-fertile and have about 5 to 6 petals per flower. Each flower produces ample pollen for good pollination. Flowers and fruit are well exposed for easy access to picking.

Pest and Disease Reactions

The new variety may not be resistant to any of the known insects and diseases common in California. It has shown to be slightly susceptible to late yellow rust, cane botrytis, fruit rot, and powdery mildew. It has not been tested for resistance to any of the root rot or virus complexes.

Isozyme in Leaf Extract

Studies of protein polymorphism in Rubus by the starch gel electrophoresis method were carried out to characterize this newly developed variety and distinguish it from similar appearing varieties.

Isozymes were extracted from young leaves and characterized, using starch gel electrophoresis techniques. The following isozymes were characterized: phosphoglucoisomerase (PGI: EC 5.3.1.9) , phosphoglucomutase (PGM:

EC 2.7.5.1) and triose phosphate isomerase (TPI: EC 5.3.1.1).

The testing used both field and greenhouse grown plant material, all grown in Watsonville, Calif. Newly mature leaves (0.5 g fresh weight) from the growing tips of the canes were used. Samples were collected in the morning, held at 4° C. and analyzed within six hours.

The tissue preparation, extraction and staining are as reported in S. Arulsekar and D. E. Parfitt, "Isozyme Analysis Procedures for Stone Fruits, Almond, Grape, Walnut, Pistachio, and Fig", HortScience 21 (4): 928–933.

Following electrophoresis, the gel was sliced and stained for each enzyme system. Banding patterns were interpreted as they developed, and gel slices were fixed in 50% glycerol.

The isozyme banding patterns of 'PS-1049', compared to 'PS-127' and 'Heritage', are given in FIG. 5. The pattern and band densities for PGI are distinctly different between 'PS-1049' and 'PS-127' and the pattern and band densities for both TPI and PGM are distinctly different between 'PS-1049' and 'Heritage'. The combination of isozyme patterns shown, derived from the specific techniques described, identify 'PS-1049' with certainty as a unique raspberry variety.

What is claimed is:

1. A new and distinct red raspberry plant known as 'PS-1049' substantially as shown and described.

* * * * *

ISOZYME BANDING PATTERNS